United States Patent [19]

Crooij et al.

[11] 4,066,664

[45] Jan. 3, 1978

[54] INTERMEDIATES FOR PREPARING α-CARBOXY-α-(3-THIENYL)PENICILLIN AND CEPHALOSPORIN DERIVATIVES

[75] Inventors: Pierre Crooij, Genval; Guy Simonet, Perwez, both of Belgium

[73] Assignee: Recherche et Industrie Therapeutiques, Belgium

[21] Appl. No.: 727,198

[22] Filed: Sept. 27, 1976

Related U.S. Application Data

[62] Division of Ser. No. 566,645, April 8, 1975, abandoned.

[51] Int. Cl.$^2$ ............................................. C07D 333/24
[52] U.S. Cl. ......................... 260/332.2 H; 260/239.1; 544/26; 544/27; 544/22; 544/30; 544/16
[58] Field of Search ................................. 260/332.2 H

[56] References Cited

PUBLICATIONS

Scheuer, J. Amer. Chem. Soc. 80: 4933–4938, (1958).
Burger, "Medicinal Chemistry" pp. 72–81, (1960).
Alles et al., J. Pharm. & Expt. Therap., 72: 265, (1941).

*Primary Examiner*—Gerald A. Schwartz
*Attorney, Agent, or Firm*—Janice E. Williams; William H. Edgerton; Alan D. Lourie

[57] ABSTRACT

A new process is disclosed for the preparation of alpha-carboxy-alpha-phenyl(or 3-thienyl)penicillin and cephalosporin derivatives.

The process comprises reacting a 1.3-dioxane-4.6-dione derivative with the desired penicillanic or cephalosporanic acid derivative.

4 Claims, No Drawings

INTERMEDIATES FOR PREPARING α-CARBOXY-α-(3-THIENYL)PENICILLIN AND CEPHALOSPORIN DERIVATIVES

This is a division of application Ser. No. 566,645 filed Apr. 8, 1975 now abandoned.

The present invention relates to a novel process for preparing alpha-carboxy-benzyl- and alpha-carboxy-3-thienylmethyl-penicillins and cephalosporins of general formula I and their pharmaceutically acceptable salts.

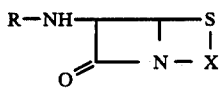

Formula I wherein
R is alpha-carboxy-alpha-phenyl (or 3-thienyl)acetyl-
X is a divalent group of formula (a) or (b)

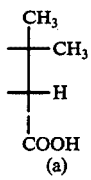
(a)

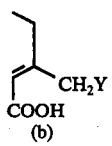
(b)

wherein Y is —OCOCH₃, hydrogen or a S-monoheterocyclic radical, e.g.

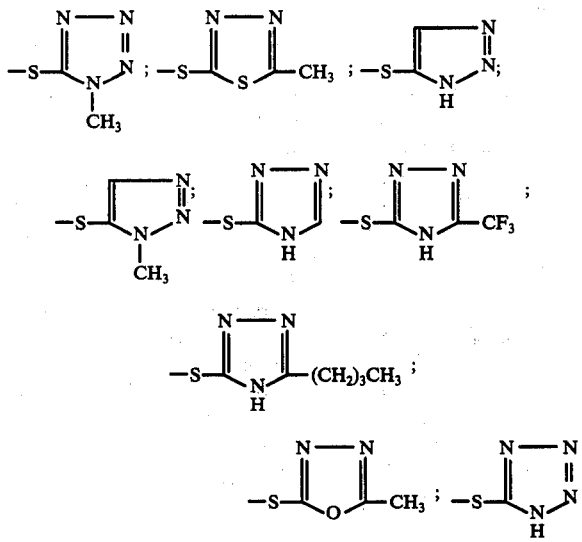

The compounds of formula I show antibacterial activity. Examples of particularly interesting compounds of formula I are 6-(α-carboxy-phenylacetamido) penicillanic acid or carbenicillin, 6-[α-carboxy-α-(3-thienyl)-acetamido]penicillanic acid or ticarcillin and 7-[α-carboxy-α-(3-thienyl)-acetamido]-3-(1-methyl-tetrazol-5-ylthiomethyl)-3-cephem-4-carboxylic acid or RIT 3838. The antibacterial activity of carbenicillin and ticarcillin is described by P. Acred et al. in Nature 215 (5096) : 25-30 (1967) and by V. Rodriguez et al. in Antimicr. Agents Chemother. 4(1), 31-6 (1973), respectively. According to Belgian Pat. No. 646 991, carbenicillin and ticarcillin are prepared from 6-aminopenicillanic acid and a reactive acid of the formula

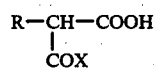

wherein R is phenyl or 3-thienyl and X represents either hydroxyl group or chlorine atom, or OR' group where R' represents a protective group—examples of which are alkyl, aryl, benzyl and substituted benzyl—which may be further eliminated.

According to U.S. Ser. No. 537,987 application filed by one of us, on Jan. 2, 1975, now abandoned RIT 3838 is prepared from activated α-carboxy-3-thienyl-acetic acid and 7-amino-3-(1-methyltetrazol-5-yl-thiomethyl)-3-cephem-4-carboxylic acid.

We have now found, and this is the object of the present invention, that it is possible to obtain the compounds of formula I when using cyclic acylals of phenyl (or 3-thienyl)malonic acids as key intermediates.

The process of the invention affords substantial advantages over the prior process by providing an easier and shorter pathway to get the compounds of formula I.

The cyclic acylals of phenyl (or 3-thienyl) malonic acids used as key intermediates in the present invention are the compounds of general formula II

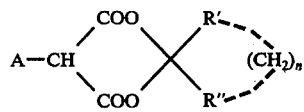

Formula II wherein
A is phenyl or 3-thienyl
R' and R" are either identical or different and, when n = 0, represent lower alkyl radicals of from 1 to 4 carbon atoms, preferably identical and representing methyl, or, when n is an integer comprised between 1 and 7, n being preferably 2 or 3, R' and R" are methylene radicals.

The products of general formula II wherein A is phenyl are described by P. J. Scheuer in J.A.C.S. 80 : 4933-4938 (1958) and by Bernd Eistert et al. Chem. Ber. 94 : 929-47 (1961). The products of formula II wherein A is 3-thienyl are novel and we have found that these 3-thienyl compounds cannot be obtained when using the sulfuric acid catalyst employed by P. J. Scheuer and B. Eistert et al. (loc.cit.) but can be obtained when using boron trifluoride etherate instead of sulfuric acid.

Prior to this invention, it was also known that a cyclic acylal of malonic acid (i.e. isopropylidene malonate or Meldrum's acid) and a cyclic acylal of methylphenyl-malonic acid (i.e. isopropylidene methylphenylmalonate) do react with substituted aniline and with benzylamine respectively (C. D. Hurd et al. in J.A.C.S. 76 : 5563-64 (1954) and P. J. Scheuer, loc.cit. to yield the corresponding malonamic acid.

The present invention provides a process for preparing a product of formula I and which comprises (1) reacting in acetic anhydride phenyl-(or 3-thienyl)-malonic acid or a functional equivalent thereof such as an ester, more particularly a di-lower alkyl ester, wherein each alkyl contains from 1 to 4 carbon atoms with a ketone selected from the group consisting of di-lower alkyl ketones (wherein the alkyl are identical or different and contains from 1 to 4 carbon atoms, each) and 5 to 10 membered cyclic ketones, preferably acetone in the presence of an acid catalyst selected from the group comprising sulfuric acid, phosphoric acid, p-toluene sulfonic acid, aluminium bromide, aluminium chloride, titanium tetrachloride and boron trifluoride etherate, preferably sulfuric acid or boron trifluoride etherate with the proviso that, when using 3-thienylmalonic acid, the catalyst is boron trifluoride etherate and (2) reacting at temperature comprised between −15° C and +30° C in an anhydrous and non-reactive organic solvent selected from the group comprising acetonitrile, dichloromethane, ethylacetate, tetrahydrofuran—preferably tetrahydrofuran the obtained product of formula II with a compound selected from the group consisting of 6-aminopenicillanic acid or 7-amino-3-acetoxymethyl-, 3-methyl- or 3-monoheterocyclicthiomethyl-3-cephem-4-carboxylic acid of formula III—preferably 7-amino-3-(1-methyltetrazol-5-ylthiomethyl)-3-cephem-4-carboxylic acid-, said compound being previously dissolved in an excess of a silyl derivative selected from the group comprising trichlormethylsilane and bis-trimethylsilylacetamide—preferably bis-trimethylsilylacetamide and (3) hydrolyzing the obtained silylated compound by adding thereto either an organic solvent selected from the group comprising of methanol, ethanol, propanol, isopropanol, butanol alone or mixed with water or acetone/water, as known to the art.

According to another embodiment of the present invention and when the intermediate 2.2-dimethyl-5-phenyl-(or 3-thienyl)-1.3-dioxane-4.6-dione is desired, step (1) of the above described process is preferably performed by allowing phenyl-(or 3-thienyl)-malonic acid to react with isopropenyl acetate in an organic solvent selected from the group comprising acetone, methylene dichloride, nitromethane and dioxane instead of allowing phenyl-(or 3-thienyl)-malonic acid to react in acetic anhydride with acetone.

In a process for preparing a product of formula I, the invention thus relates to the hereinabove defined steps which comprise reacting a product of formula II with a silylated product of formula III and hydrolyzing the obtained silylated compound.

The 6-[α-carboxy-α-phenyl (or 3-thienyl)acetamido]-penicillanic acid alkali metal salt or 7-[α-carboxy-α-(3-thienyl)-acetamido]-3-substituted-3-cephem-4-carboxylic acid alkali metal salt, preferably the disodium salt, is obtained from the acid form by extraction with dilute NaHCO₃ solution.

Our procedure is summarized in the following schema wherein A,R,R',R", X and n are as defined above.

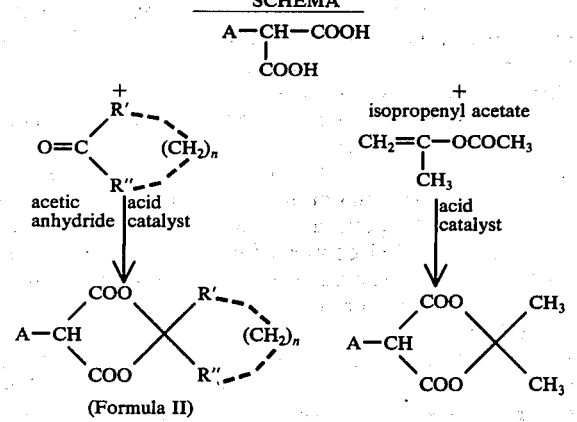

(Formula II)

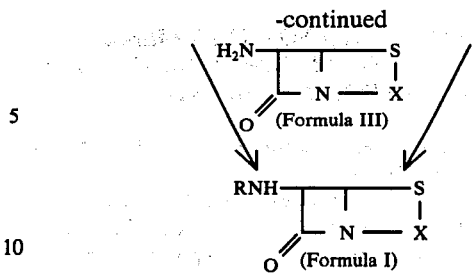

The following examples illustrate the invention but are not to be understood as limiting the scope thereof.

EXAMPLE 1

To a suspension of 1730mg (8 mmol) of 6-aminopenicillanic acid in 150 ml. of anhydrous tetrahydrofuran, there is added 6.5 ml. of bis-trimethylsilylacetamide. The mixture is stirred to give a solution to which there is added 1.76 g (8 mmol) of 2.2-dimethyl-5-phenyl-1,3-dioxane-4,6-dione (prepared according to P. J. Scheuer and S. G. Cohen in J. Amer. Chem. Soc. 80 : 4933–38 (1958). The mixture is stirred at 25° C for 3 hours.

Methanol (50 ml.) is added thereto and the solution is stirred for 15 minutes. The solvents are removed under reduced pressure and the residue is taken up with 100 ml. of water, brought to pH 2.5 with 0.5ml. 6NHCl and extracted three times with 50 ml. of ethyl acetate. The organic layer is dried over anhydrous sodium sulfate, decanted, decolorized with charcoal and then filtered. Most of the solvent is evaporated under reduced pressure and 150 ml. of petroleum ether (50°–70°) is added thereto.

The suspension is stirred for 15 minutes and filtered. The precipitate is washed and dried over anhydrous $P_2O_5$ under reduced pressure to yield 6-(α-carboxy-α-phenylacetamido) penicillanic acid (carbenicillin).

An aliquot of the obtained compound (1.55 g-4 mmol) is dissolved in 100 ml. of ethylacetate and the solution is extracted with 10 ml., 30 ml., 50 ml., 30 ml. and 10 ml. portions of 0.1 N NaHCO₃.

The three first fractions are pooled together and lyophilized to yield the disodium salt of 6-(α-carboxy-α-phenylacetamido)penicillanic acid.

$R_f$ = 0.51 (± 0.1) in the system chloroform/acetonitrile/water/formic acid (35/68/5/2).

nmr (D₂O) : 7.53 s (5H); 5.66 m (1H + 1H); 4.34 m (1H) appears as 2 singlets corresponding to 50 % of D and 50 % of L isomer, respectively; and 1.58 m (3H + 3H).

EXAMPLE 2

To a suspension of 9 g (50 mmol) of phenylmalonic acid in 23 ml. of acetic anhydride there is added 0.5 ml. of concentrated H₂SO₄. The mixture is stirred to give a solution to which there is added at once 7.5 ml. (83 mmol) of 2-butanone, the mixture being stirred at 25° C for 1 hour and then maintained at −15° C for 60 hours.

Water (250 ml.) is then added thereto and the mixture is stirred for 30 minutes. The obtained precipitate is washed with 250 ml. of water up to pH 6.5, dried under reduced pressure and dissolved in 100 ml. of chloroform. The organic solution is dried over anhydrous sodium sulfate; most of the solvent is evaporated under reduced pressure and 100 ml. of petroleum ether (50°–70° C) is added thereto. The suspension is stirred for 30 minutes and filtered. The precipitate is washed with 20 ml. of petroleum ether (50°–70° C) and dried over P$_2$O$_5$ under reduced pressure to yield 2-ethyl-2-methyl-5-phenyl-1.3-dioxane-4.6-dione. m.p. 135–6° C.

R$_f$ = 0.88 (± 0.1) in acetone : detection with bromocresol green and KMnO$_4$.

nmr (CDCl$_3$) 7.38 s (5H), 4.78 s (splitting) (1H), 2.02 q (splitting) (2H, J = 7.3 cps), 1.71 s (splitting) (3H), 1.08 t (3H, J = 7.3 cps).

EXAMPLE 3

When 2-butanone is substituted by cyclopentanone in the example 2 and the procedure described therein carried out, 2.2-tetramethylene-5-phenyl-1.3-dioxane-4.6-dione is obtained. m.p. 155–6° C.

R$_f$ = 0.90 (± 0.1) in acetone; detection with bromocresol green and KMnO$_4$.

nmr (DMSO-d$_6$) 7.44 s (5H), 4.75 s (1H), 2.25 m (4H), 1.85 m (4H).

EXAMPLE 4

When an equivalent amount of 2-ethyl-2-methyl-5-phenyl-1.3-dioxane-4.6-dione as prepared in the example 2 is substituted for 2.2-dimethyl-5-phenyl-1.3-dioxane-4.6-dione and the reaction with 6-aminopenicillanic acid is carried out as disclosed in the example 1, 6-(α-carboxy-α-phenylacetamido)penicillanic acid (carbenicillin) is obtained.

EXAMPLE 5

When an equivalent amount of 2.2-tetramethylene-5-phenyl-1.3-dioxane-4.6-dione prepared in the example 3 is substituted for 2.2-dimethyl-5-phenyl-1.3-dioxane-4.6-dione and the reaction with 6-aminopenicillanic acid is carried out as disclosed in the example 1, 6-(α-carboxy-α-phenylacetamido)penicillanic acid (carbenicillin) is obtained.

EXAMPLE 6

To a suspension of 3 g (16 mmol) of 3-thiophenemalonic acid in 3.5 ml. of acetic anhydride there is added 0.15 ml. of boron trifluoride etherate (corresponding to 48 % of BF$_3$). The mixture is stirred for 30 minutes to give a solution to which there is added at once and 0° C 3 ml of acetone. The mixture is stirred at 25° C for 1 hour and maintained at −15° C for 12 hours.

Ice water (20 ml.) is then added thereto and the mixture is stirred for 15 minutes and filtered.

The obtained precipitate is taken up in chloroform (50 ml.), the organic layer is dried over anhydrous sodium sulfate and filtered on DARCO G60 (a product manufactured and sold by Atlas Chem. Ind., New Murphy Road, Wilmington, DEL 19899)—charcoal. Most of the solvent is evaporated under reduced pressure and 50 ml. of petroleum ether (50°–70° C) is added thereto. The suspension is stirred for 15 minutes and filtered. The precipitate is washed with 20 ml. of petroleum ether (50°–70° C) and dried over anhydrous P$_2$O$_5$ under reduced pressure to yield 2.2-dimethyl-5-(3-thienyl)-1.3-dioxane-4.6-dione. m.p. (decomposition) 128°–130° C. 7

R$_f$ = 0.90 (±0.1) in the system acetonitrile/water (8/2) detection with bromocresol green and KMnO$_4$; U.V. detection.

nmr (CD$_3$CN) 7.46 m (2H), 7.10 m (1H), 5.35 m (1H), 1.81 s (6H).

EXAMPLE 7

To 11.8 g (50 mmol) of phenylmalonic acid diethyl ester in 23 ml. of acetic anhydride there are added 0.5 ml. of concentrated H$_2$SO$_4$ and 20 ml. of acetone. The mixture is stirred at 25° C for 8 hours, water (250 ml.) is then added thereto and the mixture is stirred for 30 minutes. The obtained precipitate is washed with 250 ml. of water up to pH 6.5, dried under reduced pressure and dissolved in 100 ml. of chloroform. The organic solution is dried over anhydrous sodium sulfate, most of the solvent is evaporated under reduced pressure and 100 ml. of petroleum ether (50°–70° C) is added thereto. The suspension is stirred for 30 minutes and filtered. The precipitate is washed with 20 ml. of petroleum ether (50°–70° C) and dried over P$_2$O$_5$ under reduced pressure to yield 2.2-dimethyl-5-phenyl-1.3-dioxane-4.6-dione with the same characteristics as the compound described by P. J. Scheuer in J.A.C.S. 80, 4933–38 (1958).

EXAMPLE 8

When an equivalent amount of phenylmalonic acid is substituted in the procedure of example 6 for 3-thiophenemalonic acid and the reaction with 6-aminopenicillanic acid is carried out as disclosed in the example 1, 6-(α-carboxy-α-phenylacetamido)penicillanic acid (carbenicillin) is obtained.

EXAMPLE 9

To 13.02 g of 1-methyl-5-mercapto-1,2,3,4-tetrazole prepared according to the procedure described by Stollé R. et al. in J. Prakt. Chem. [2], 124, 261–79 (1930) and dissolved in 800 ml. of a 0.2 M phosphate buffer solution (pH 6.5–6.6), there is added 20.4 g of 7-aminocephalosporanic acid (7-ACA). The mixture is brought to pH 6.3–6.6 by addition of 21.5 ml. of triethylamine, heated at 70° C for 80 minutes, at once cooled to 20° C, acidified to pH 3.5 by addition of 65 ml. of 2N HCl and then stirred for 15 minutes.

The obtained precipitate is filtered, washed with 200 ml. of water, 200 ml. of methanol and 200 ml. of diethylether and dried under reduced pressure to yield a crude product which is dissolved in 300 ml. of 2N HCl, treated with DARCO G60 (a product manufactured and sold by Atlas Chem. Ind.)-charcoal and filtered.

Crystallization occurs from the filtrate brought to pH 3.7 by addition of 45 ml. of concentrated ammonium hydroxide.

The crystallization medium is stirred for 30 minutes at 25° C and filtered under reduced pressure. The precipitate is washed with 200 ml. of water, 200 ml. of methanol and 200 ml. of diethylether and dried at 40° C over P$_2$O$_5$ under reduced pressure to yield 7-amino-3-(1-methyltetrazol-5-ylthiomethyl)-3-cephem-4-carboxylic acid.

R$_f$ = 0.44 (± 0.10) in the system acetonitrile/water (80/20), detection with U.V. or bromocresol green.

nmr (D$_2$O—Na$_2$CO$_3$) 5.48 d (1H) (J 4.7 c./sec.), 5.08 d (1H) (J 4.7 c./sec.), 4.40 and 4.06 2d (2 × 1H) (J 13 c./sec.), 3.95 s (3H), 3.86 and 3.43 2d (2 × 1H) (J 18 c./sec.).

EXAMPLE 10

To a suspension of 656.7 mg (2 mmol) of 7-amino-3-(1-methyltetrazol-5-ylthiomethyl)-3-cephem-4-carboxylic acid (as prepared in example 9) in 25 ml. of anhydrous tetrahydrofuran there is added 1.6 ml. of bis-trimethylsilylacetamide. The mixture is stirred to give a solution to which there is added at once 452.5 mg (2 mmol) of 2.2-dimethyl-5-(3-thienyl)-1.3-dioxane-4.6-dione as prepared in example 6, the mixture being stirred at 25° C for 8 hours. Tetrahydrofuran is removed under reduced pressure and the residue is taken up with 30 ml. of water, brought to pH 2.5 with 0.5 ml. 6N HCl, stirred for 15 minutes and extracted three times with 25 ml. of ethyl acetate. The organic layer is dried over anhydrous sodium sulfate and filtered over DARCO G60 (a product manufactured and sold by Atlas Chem. Ind.)-charcoal. Most of the solvent is evaporated under reduced pressure and 100 ml. of petroleum ether (50°–70° C) is added thereto. The suspension is stirred for 30 minutes and filtered. The precipitate is washed with 20 ml. of petroleum ether (50°–70° C) and dried over anhydrous $P_2O_5$ under reduced pressure to yield DL-7-[α-carboxy-α-(3-thienyl)-acetamido]-3-(1-methyl-tetrazol-5-ylthiomethyl)-3-cephem-4-carboxylic acid (RIT 3838).

nmr ($CD_3OD$): 7.70–7.25 m (3H), 5.85 d (1H, J = 5.1 cps) 5.19 d (1H, J = 5.1 cps), 4.42 m (2H), 4.06 s (3H), 3.77 m (2H).

$R_f$ = 0.55 (± 0.10) in the system chloroform/acetonitrile/water/formic acid) (35/58/5/2), detection with U.V.

EXAMPLE 11

To a suspension of 432.56 mg (2 mmol) of 6-aminopenicillanic acid in 40 ml. of anhydrous tetrahydrofuran, there is added 1.5 ml. of bis-trimethylsilylacetamide, the mixture being stirred at 25° C for 12 hours.

To the solution there is added at once 452.5 mg (2 mmol) of 2.2-dimethyl-5-(3-thienyl)-1.3-dioxane-4.6-dione, as prepared in example 6, the mixture being stirred at 25° C for 4 hours. When reaction is carried out as disclosed in the example 10, 6-[α-carboxy-α-(3-thienyl) acetamido]penicillanic acid (ticarcillin) is obtained.

$R_f$ = 0.62 (± 0.1) in the system acetonitrile/water (8/2) U.V. detection, detection with bromocresol green and $KMnO_4$.

nmr (($CD_3$)$_2CO$): 8.77 m deuterated with $D_2O$ (2 × COOH), 8.15 m deuterated with $D_2O$ (—NH—), 7.75–7.25 m (3H), 5.72 m (2H), 5.00 s deuterated with $D_2O$ (1H), 4.40 s (1H), 1.57 s (6H).

EXAMPLE 12

When an equivalent amount of 7-amino-3-heterocyclic thiomethyl-3-cephem-4-carboxylic acid listed below is substituted in the procedure of example 10 for 7-amino-3-(1-methyltetrazol-5-ylthiomethyl)-3-cephem-4-carboxylic acid, the appropriate α-carboxy-α-(3-thienyl)-acetamido-3-heterocyclicthiomethyl-3-cephem-4-carboxylic acid is obtained.

7-amino-3-(5-methyl-1,3,4-thiadiazol-2-ylthiomethyl)-3-cephem-4-carboxylic acid
7-amino-3-(1,2,3-triazol-5-ylthiomethyl)-3-cephem-4-carboxylic acid
7-amino-3-(1-methyl-1,2,3-triazol-5-ylthiomethyl)-3-cephem-4-carboxylic acid
7-amino-3-(1,3,4-triazol-2-ylthiomethyl)-3-cephem-4-carboxylic acid
7-amino-3-(5-trifluoromethyl-1,3,4-triazol-2-ylthiomethyl)-3-cephem-4-carboxylic acid
7-amino-3-(5-n-butyl-1,3,4-triazol-2-ylthiomethyl)-3-cephem-4-carboxylic acid
7-amino-3-(5-methyl-1,3,4-oxadiazol-2-ylthiomethyl)-3-cephem-4-carboxylic acid
7-amino-3-(1,2,3,4-tetrazol-5-ylthiomethyl)-3-cephem-4-carboxylic acid

EXAMPLE 13

To a solution of 3.72 g (20 mM) 3-thienylmalonic acid in 2.54 ml. (23.3 mM) isopropenylacetate and 5 ml. acetone there is added with stirring 0.37 ml. of boron trifluoride etherate. The mixture is stirred at 0° C for 8 hours and maintained at −15° C for 15 hours, diluted with 30 ml. of carbon tetrachloride and then filtered. The precipitate is washed with 50 ml. of ether and dried under reduced pressure to yield the same compound as described in the example 6.

EXAMPLE 14

When an equivalent amount of 7-amino cephalosporanic acid is substituted in the procedure of example 10 for 7-amino-3-(1-methyltetrazol-5-ylthiomethyl)-3-cephem-4-carboxylic acid, 7-[α-carboxy-α-(3-thienyl)-acetamido]cephalosporanic acid is obtained.

EXAMPLE 15

When an equivalent amount of 7-amino-3-desacetoxy cephalosporanic acid is substituted in the procedure of example 10 for 7-amino-3-(1-methyltetrazol-5-ylthiomethyl)-3-cephem-4-carboxylic acid, 7-[α-carboxy-α-(3-thienyl)-acetamido]-3-desacetoxy cephalosporanic acid is obtained.

We claim:

1. A compound of the formula:

$$A-CH\begin{matrix} COO \\ \\ COO \end{matrix}\begin{matrix} R' \\ \\ R'' \end{matrix}(CH_2)_n$$

wherein:

A is 3-thienyl; and
R' and R" are either identical or different and, when n = 0, represent lower alkyl radicals of from 1 to 4 carbon atoms, or, when n is an integer between 1 and 7, R' and R" are methylene radicals.

2. A compound according to claim 1 wherein R' and R" are either identical or different lower alkyl radicals of from 1 to 4 carbon atoms and n = 0.

3. A compound according to claim 1 wherein R' and R" are either identical or different methylene radicals and n is an integer between 1 and 7.

4. A compound according to claim 2, said compound being 2,2-dimethyl-5-(3-thienyl)-1,3-dioxane-4,6-dione.

* * * * *